United States Patent
Tepper et al.

(10) Patent No.: US 10,390,702 B2
(45) Date of Patent: Aug. 27, 2019

(54) IMPLANTABLE DEVICES AND METHODS FOR THE EVALUATION OF ACTIVE AGENTS

(71) Applicant: Kibur Medical, Inc., Boston, MA (US)

(72) Inventors: Robert I. Tepper, Weston, MA (US); Jason Fuller, Boston, MA (US); Oliver Jonas, Weston, MA (US); John Santini, Chanhassan, MN (US)

(73) Assignee: Kibur Medical, Inc., Boston, MA (US)

( * ) Notice: Subject to any disclaimer, the term of this patent is extended or adjusted under 35 U.S.C. 154(b) by 93 days.

(21) Appl. No.: 15/077,300

(22) Filed: Mar. 22, 2016

(65) Prior Publication Data

US 2016/0198989 A1    Jul. 14, 2016

Related U.S. Application Data

(63) Continuation of application No. 13/729,738, filed on Dec. 28, 2012.
(Continued)

(51) Int. Cl.
*A61B 5/00* (2006.01)
*B33Y 80/00* (2015.01)
(Continued)

(52) U.S. Cl.
CPC .......... *A61B 5/0017* (2013.01); *A61B 5/4848* (2013.01); *A61B 5/6851* (2013.01);
(Continued)

(58) Field of Classification Search
CPC ... G01N 33/5008; A61M 5/00; A61K 9/0097; A61B 5/0084; A61B 5/6861
See application file for complete search history.

(56) References Cited

U.S. PATENT DOCUMENTS 5,139,832 A    8/1992  Hayashi
5,189,110 A    2/1993  Ikematu
(Continued)

FOREIGN PATENT DOCUMENTS

CA    2696209    2/2009
EP    0153070    8/1985
(Continued)

OTHER PUBLICATIONS

Bates, et al., "New amorphous thin-film lithium electrolyte and rechargeable microbattery", IEEE 35th International Power Sources Symposium, 337-39 (1992).
(Continued)

*Primary Examiner* — Bradley J Osinski
(74) *Attorney, Agent, or Firm* — PABST Patent Group LLP

(57) ABSTRACT

Devices for the local delivery of microdose amounts of one or more active agents, alone or in combination, in one or more dosages, to selected tissue of a patient are described. The devices generally include multiple microwells arranged on or within a support structure. The microwells contain one or more active agents, alone or in combination, in one or more dosages and/or release pharmacokinetics. In an exemplary embodiment, the device has a cylindrical shape, having symmetrical wells on the outside of the device, each well containing one or more drugs, at one or more concentrations, sized to permit placement using a catheter, cannula, or stylet. Optionally, the device has a guidewire, and fiber optics, sensors and/or interactive features such as remote accessibility (such as WiFi) to provide for in situ retrieval of information and modification of device release properties. In the most preferred embodiment, the fiber optics and/or sensors are individually accessible to discrete wells.

17 Claims, 5 Drawing Sheets

Related U.S. Application Data

(60) Provisional application No. 61/582,009, filed on Dec. 30, 2011.

(51) Int. Cl.
*A61K 9/00* (2006.01)
*A61M 5/00* (2006.01)
*G01N 33/50* (2006.01)
*A61B 10/02* (2006.01)
*A61B 10/04* (2006.01)

(52) U.S. Cl.
CPC ........ *A61B 10/0266* (2013.01); *A61K 9/0097* (2013.01); *A61M 5/00* (2013.01); *B33Y 80/00* (2014.12); *G01N 33/5008* (2013.01); *A61B 5/0084* (2013.01); *A61B 5/6861* (2013.01); *A61B 2010/045* (2013.01); *A61B 2562/12* (2013.01); *F04C 2270/041* (2013.01)

(56) References Cited

U.S. PATENT DOCUMENTS

| | | | |
|---|---|---|---|
| 5,733,925 | A | 3/1998 | Kunz et al. |
| 6,428,504 | B1 | 8/2002 | Rieziat |
| 6,527,762 | B1 | 3/2003 | Santini, Jr. |
| 6,611,707 | B1 | 8/2003 | Prausnitz |
| 6,692,456 | B1 | 2/2004 | Eppstein et al. |
| 6,808,522 | B2 | 10/2004 | Richards |
| 8,349,554 | B2 | 1/2013 | Bahrami |
| 8,475,412 | B2 | 7/2013 | Bahrami |
| 8,657,786 | B2 | 2/2014 | Bahrami |
| 8,672,887 | B2 | 3/2014 | Bahrami |
| 8,834,428 | B2 | 9/2014 | Bahrami |
| 2006/0058966 | A1 | 3/2006 | Bruckner |
| 2006/0079740 | A1 | 4/2006 | Silver |
| 2006/0094985 | A1 | 5/2006 | Aceti et al. |
| 2006/0163215 | A1 | 7/2006 | Maenosono |
| 2007/0016163 | A1* | 1/2007 | Santini, Jr. .......... A61C 8/0012 604/500 |
| 2007/0275035 | A1 | 11/2007 | Herman |
| 2008/0108959 | A1 | 5/2008 | Jung et al. |
| 2009/0130167 | A1 | 5/2009 | Shelton |
| 2012/0109104 | A1 | 5/2012 | Bahrami |
| 2012/0121514 | A1 | 5/2012 | Bahrami et al. |
| 2012/0265064 | A1 | 10/2012 | Bahrami |
| 2012/0296206 | A1 | 11/2012 | Bahrami |
| 2013/0184593 | A1 | 7/2013 | Tepper |
| 2014/0162360 | A1 | 6/2014 | Bahrami |
| 2014/0162901 | A1 | 6/2014 | Bahrami |
| 2014/0309530 | A1 | 10/2014 | Chono |
| 2014/0309590 | A1 | 10/2014 | Bahrami et al. |

FOREIGN PATENT DOCUMENTS

| | | |
|---|---|---|
| EP | 1938852 | 7/2008 |
| GB | 1462958 | 1/1977 |
| WO | 9800107 | 1/1998 |
| WO | 0074767 | 12/2000 |
| WO | WO 00/74767 | 12/2000 |
| WO | 200230264 | 4/2002 |
| WO | 02054941 | 7/2002 |
| WO | 2002054941 | 7/2002 |
| WO | 2004033034 | 4/2004 |
| WO | 2004033036 | 4/2004 |
| WO | 2004047907 | 6/2004 |
| WO | WO 2004047907 | 6/2004 |
| WO | 2004091714 | 10/2004 |
| WO | 2005025413 | 3/2005 |
| WO | WO 2005/025413 | 3/2005 |
| WO | 2008008557 | 1/2008 |
| WO | WO 2008/008557 | 1/2008 |
| WO | WO 2008010681 | 1/2008 |
| WO | 2010022252 | 2/2010 |

OTHER PUBLICATIONS

Fire, et al, "Potent and specific genetic interference by double-stranded RNA in Caenorhabditis elegans", Nature, 391:806-11 (1998).

Laske, et al., "Efficacy of direct intratumoral therapy with targeted protein toxins for solid human glkiomas in nude mice", J Neurosurg., 80:520-6 (1994).

Sheu, et al., "Small hepatocellular carcinoma: intratumor ethanol treatment using new needle and guidance systems", Radiology, 163:43-8 (1987).

Weissleder, et al., "In vivo imaging of tumors with protease-activated near-infrared fluorescent probes", Nature, 17:375-8 (1999).

Jonas, et al., "An implantable microdevice to perform high-throughput in vivo drug sensitivity testing in tumors". Sci Transl Med., 7(284):1-12 (2015).

Oudin, et al., "Tumor-cell-driven extracellular matrix remodeling drives haptotaxis during metastatic progression", Cancer Discovery, 6:516-31 (2016).

Bates, et al., "New amorphous thin-film lithium electrolyte and rechargeable microbattery", IEEE 35th International Power Sources Symposium, 337w 39 (1992).

Di Masi, et al., "The Price of Innovation: New Estimates of Drug Development Costs", J. Hlth. Econ., 22; 151-185 (2003).

Fire, et ai, "Potent and specific genetic interference by double-stranded RNA in Caenorhabditis elegans", Nature, 391 ;806-11 (1998).

Jones and Akridge, "Development and performance of a rechargeable thin-film solid-state microbattery", J Power Sources, 54:63-67 (1995).

Japanese Office Action dated Aug. 23, 2017.

Japanese Office Action dated Oct. 25, 2018.

Jonas, et al., "Parallel in Vivo Assessment of Drug Phenotypes at Various Time Points during Systemic BRAF Inhibition Reveals Tumor Adaptation and Altered Treatment Vulnerabilities", Clin Cancer Res., Apr. 18. [Epub ahead of print] pp. 1-8 (2016).

* cited by examiner

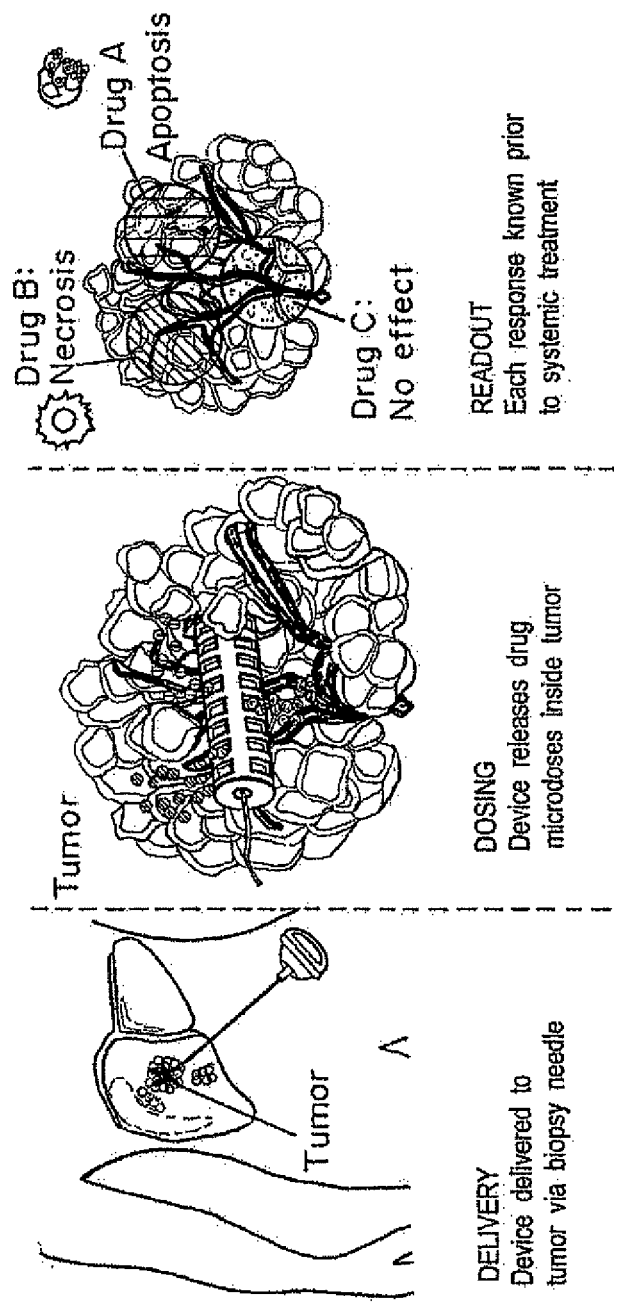

1. TUMOR CELL INJECTION   FIG. 5
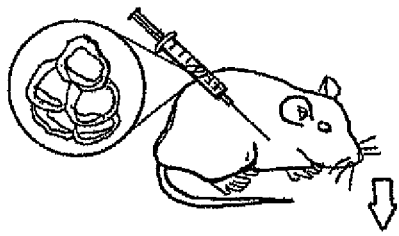
2. ESTABLISH TUMOR
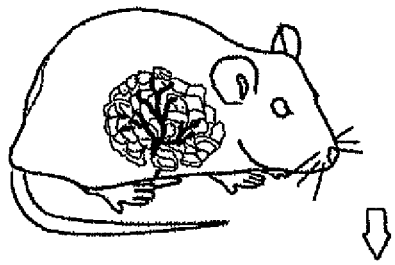
3. SYSTEMIC PHARMACOLOGICAL STUDIES
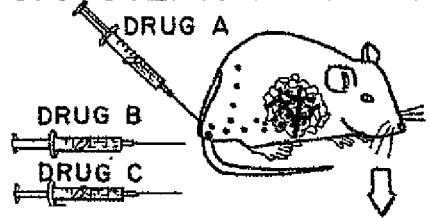
4. DEVICE IMPLANTATION/MICRODOSING
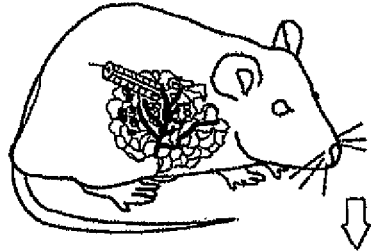
5. CORRELATION OF SYSTEMIC AND MICRODOSING DATA
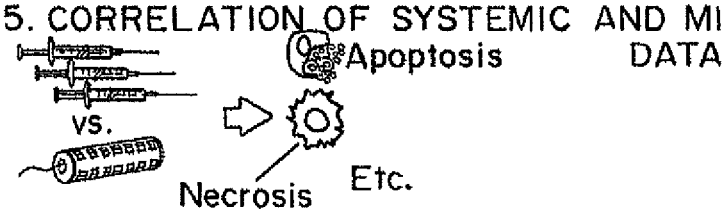

IMPLANTABLE DEVICES AND METHODS FOR THE EVALUATION OF ACTIVE AGENTS

CROSS REFERENCE TO RELATED APPLICATION

This application is a continuation of U.S. application Ser. No. 13/729,738, filed Dec. 28, 2012, which claims the benefit of and priority to U.S. Provisional Application No. 61/582,009 entitled "Implantable Devices and Methods for the Evaluation of Active Agents" by Robert I. Tepper, Jason Fuller, Oliver Jonas, and John Santini, filed on Dec. 30, 2011, and where permissible are incorporated by reference in their entireties.

FIELD OF THE INVENTION

The invention is generally related to devices, methods, systems, and kits for the evaluation of therapeutic agents in situ within tissues to be treated in patients.

BACKGROUND OF THE INVENTION

In recent years, research has demonstrated that the progression of many diseases is governed by molecular and genetic factors which are patient specific. For example, it is now understood that cancer is driven by diverse genetic and epigenetic factors which are often patient specific. As a result, disease progression and anti-cancer drug response is unique to every patient. In spite of this understanding, most clinical treatments still follow established standard-of-care guidelines and paradigms which fail to account for patient-specific factors.

Personalizing therapeutic treatments in view of the patient-specific molecular and genetic factors offers the opportunity to improve therapeutic outcomes. In order to tailor treatments in a patient specific fashion, tools and methods of predicting and/or rapidly determining the response of a patient to particular drug regimens are needed.

Therefore, it is an object of the invention to provide devices that can be used to locally deliver discrete microdose quantities of one or more active agents to tissues in a patient, and which can be easily removed with tissue remaining spatially positioned relative to the discrete dosages of active agent.

It is also an object of the invention to provide methods for the facile, in vivo, analysis of the sensitivity of a disease or disorder in a patient to one or more active agents.

SUMMARY OF THE INVENTION

Devices for the local delivery of microdose amounts of one or more active agents, alone or in combination, in one or more dosages, to selected tissue of a patient are described. The devices generally include multiple microwells arranged on or within a support structure. The microwells contain one or more active agents, alone or in combination, in one or more dosages and/or release pharmacokinetics. In certain embodiments, the devices are configured to facilitate implantation and retrieval in a target tissue. In an exemplary embodiment, the device has a cylindrical shape, having symmetrical wells on the outside of the device, each well containing one or more drugs, at one or more concentrations. The device is sized to permit placement using a catheter, cannula, or stylet. In a preferred embodiment, the device has a guidewire to assist in placement and retrieval. The device may also include features that assist in maintaining spatial stability of tissue excised with the device, such as fins or stabilizers that can be expanded from the device prior to or at the time of removal. Optionally, the device has fiber optics, sensors and/or interactive features such as remote accessibility (such as WiFi) to provide for in situ retrieval of information and modification of device release properties. In the most preferred embodiment, the fiber optics and/or sensors are individually accessible to discrete wells.

The devices are formed of biocompatible silicon, metal, ceramic or polymers. They may include materials such as radioopaque materials or materials that can be imaged using ultrasound or MM. They can be manufactured using techniques such as deep ion etching, nano imprint lithography, micromachining, laser etching, three dimensional printing or stereolithography. Drug can be loaded by injection of a solution or suspension into the wells followed by solvent removal by drying, evaporation, or lyophilization, or by placement of drug in tablet or particulate form into the wells. Drug release pharmacokinetics are a function of drug solubility, excipients, dimensions of the wells, and tissue into which the device is implanted (with greater rate of release into more highly vascularized tissue, than into less vascular tissue).

In certain embodiments, the devices are implanted directly into a solid tumor or tissue to be biopsied. Upon implantation, the devices locally release an array of active agents in microdoses. Subsequent analysis of tumor response to the array of active agents can be used to identify particular drugs, combinations of drugs, and/or dosages that are effective for treating a solid tumor in a patient. By locally delivering microdoses of an array of drugs, the microassay device can be used to test patients for response to large range of regimens, without inducing systemic toxicities, quickly and under actual physiological conditions. These data are used, optionally in combination with genomic data, to accurately predict systemic drug response.

BRIEF DESCRIPTION OF THE DRAWINGS

FIGS. 4A-D are schematics showing the arrangement of drugs in wells in the device (FIG. 4A), implantation (FIG. 4B), dosing where drug is released from the wells (FIG. 4C), and the different results obtained (FIG. 4D).

FIG. 5 is a schematic showing testing of the device in mice.

DETAILED DESCRIPTION OF THE INVENTION

Figure 1:
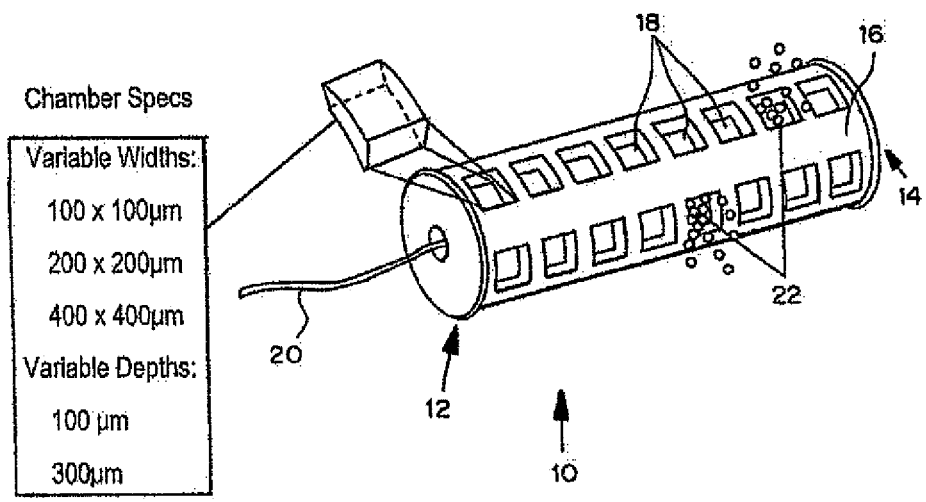
FIG. 1 is a perspective view of a cylindrical device containing a guidewire attached to the proximal end of the cylindrical device.

Devices and methods of use thereof are provided. Devices include one or more microwells which contain one or more active agents, in one or more different dosages. The reservoir locally delivers a microdose amount of an active to a target tissue located proximally to the microwell.

I. Definitions

"Microwell," as used herein, refers to a chamber, void, or depression formed within or on the support structure.

"Support Structure," as used herein, refers to the body of the device to which one or more microwells are attached or within which one or more microwells are formed.

"Guidewire," as used herein, refers to a wire-like structure attached to the device which is intended to assist in the implantation of the device at a site of medical interest and/or its subsequent removal from the site of implantation.

"Active Agent," as used herein, refers to a physiologically or pharmacologically active agent that can act locally and/or systemically in the body. The term "active agent" includes agents that can be administered to a subject for the treatment (e.g., therapeutic agent), prevention (e.g., prophylactic agent), or diagnosis (e.g., diagnostic agent) of a disease or disorder. "Anti-neoplastic agent", as used herein, refers to an active agent that either inhibits the growth and multiplication of neoplastic cells, such as by interfering with the cell's ability to replicate DNA, and/or is cytotoxic to neoplastic cells.

"Effective amount" or "therapeutically effective amount", as used herein, refers to an amount of one or more therapeutic agents which is effective to decrease the size of a solid tumor or to inhibit the growth of a solid tumor.

"Biocompatible" and "biologically compatible", as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

"Biodegradable Polymer" and "Bioerodible Polymer" are used herein interchangeably, and generally refers to a polymer that will degrade or erode by enzymatic action or hydrolysis under physiologic conditions to smaller units or chemical species that are capable of being metabolized, eliminated, or excreted by the subject. The degradation time is a function of polymer composition, morphology, such as porosity, particle dimensions, and environment. Suitable degradation times are from hours to weeks, more preferable from days to weeks. "Tumor," as used herein, refers to an abnormal mass of tissue that results from the proliferation of cells. Typically, solid tumors do not contain cysts or liquid areas within the tissue mass. Solid tumors can arise in any part of the body, and may be benign (not cancerous) or malignant (cancerous). Most types of cancer other than leukemias can form solid tumors. Solid tumors include, for example, adenocarcinomas, carcinomas, hemangiomas, liposarcomas, lymphomas, melanomas and sarcomas.

"Tissue," as used herein, refers to groups of cells that perform a particular function, as well as organs, which are aggregates of tissues.

"Local Delivery" and "Local Administration," as generally used herein, refer to the administration of an active agent to a target tissue location from a source that is at the target tissue location, or adjacent to or in close proximity to the target tissue location.

"Microdose," as used herein, refers to an amount of an active agent that is locally administered to a tissue to determine one or more clinical parameters, such as efficacy of active agent, the metabolism of the active agent, or a combination thereof.

II. Devices

Support Structure

Devices generally include one or more microwells formed on or within a support structure. The support structure forms the body of the device. The support structure can be fabricated to form devices having a variety of shapes. For example, the device can be cuboid, cubic, or cylindrical in shape. In the preferred embodiment, the device is cylindrical. The support structure may also be configured to have one or more areas of separation. For example, depending on such factors as the material used and number of microwells, the areas of separation may include perforations, a material of enhanced flexibility or lower durometer, hinges, joints, etc., which allow portions of the support structure to be separated or flex.

Preferably, the dimensions of the device are suitable to allow for implantation using an 18 gauge biopsy needle, stylet, cannula or catheter. In certain embodiments, the cylindrical device has a diameter of between about 0.5 mm and about 2 mm, more preferably between about 0.5 mm and about 1.5 mm, most preferably between about 0.5 mm and about 1.0 mm. In a particular embodiment, the cylindrical device has a diameter of approximately 0.9 mm. In certain embodiments, the cylindrical device has a length of less than about 5 mm, more preferably less than about 4 mm, most preferably less than about 3 mm. In a particular embodiment, the cylindrical device has a length of approximately 2.5 mm.

Microwells

The surface of the device includes one or more microwells, each of which typically includes a solid bottom proximal to the support structure, one or more solid side walls, and an opening located on the surface of the device distal to the support structure. Alternatively, the microwells can be in the form of a hemispherical bowl.

Devices can contain any number of microwells. In the device shown in the attached figures, wells are provided in five rows of eight wells. Representative numbers of microwells range from four to about 100. The microwells may have any shape (e.g., circular or rectangular) and dimensions (e.g., length/width, diameter, and/or depth) suitable for a particular application. In some embodiments, all of the microwells in a device have the same shape and dimensions. In these cases, all of the microwells in the device have substantially the same volume. In other embodiments, the array contains microwells with multiple shapes, dimensions, or combinations thereof. In these cases, microwells with a variety of volumes may be incorporated into a single device.

The microwells can have any suitable shape. For example, the microwells can be circular, ovoid, quadrilateral, rectangular, square, triangular, pentagonal, hexagonal, heptagonal, or octagonal. In some embodiments, the microwells are rectangular in shape. In these instances, the shape of the microwells can be defined in terms of the length of the four side walls forming the perimeter of the rectangular microwell.

In certain instances, the rectangular microwells have side walls ranging from about 50 microns to about 500 microns in length, more preferably from about 100 microns to about 400 microns in length. In particular embodiments, the four side walls forming the perimeter of the rectangular microwell are of substantially equivalent length (i.e., the microwell has a square shape). Preferred sizes are 100×100, 200×200, and 400×400 microns, with depths of 100 to 300 microns.

In some embodiments, the microwells are spherical in shape. In certain instances, the spherical microwells have diameters ranging from about 50 microns to about 500 microns, more preferably from about 100 microns to about 400 microns.

The depth of the microwells, governed by the height of the solid side walls forming the microwells, can vary to provide microwells having the desired volume and/or volume-to-surface-area ratio for particular applications. In certain instances, the depth of the microwells ranges from about 50 microns to about 500 microns, more preferably from about 75 microns to about 400 microns, most preferably from about 100 to about 300 microns.

The microwells may have any volume suitable for a particular application. In certain instances, the volume of the microwells ranges from about $1.25 \times 10^5$ cubic microns to about $1.25 \times 10^8$ cubic microns, more preferably from about $1.00 \times 10^5$ cubic microns to about $6.40 \times 10^7$ cubic microns, most preferably from about $1.00 \times 10^5$ cubic microns to about $4.80 \times 10^7$ cubic microns.

The microwells may be arranged on or within the support structure in a variety of geometries depending upon the overall device shape. For example, in some embodiments, the microwells are arranged on or within the support structure with the axes of the microwells relatively parallel and the distal openings in a relatively single plane. In this configuration the microwells can be arranged in rectangular or circular arrays. Alternatively, the microwells may be arranged in a three-dimensional pattern where the distal ends of the microwells lie in multiple planes. In this three-dimensional pattern the axes of the microwells may be relatively parallel or be skewed relative to one another, depending on the overall shape of the device.

The microwells may be equally spaced from one another or irregularly spaced. In preferred embodiments, the edges of neighboring microwells are separated by at least about 50 microns, more preferably at least about 75 microns, most preferably at least about 100 microns. In certain embodiments, the edges of neighboring microwells are separated by at least about 100 microns, about 200 microns, about 300 microns, or about 400 microns.

Materials Used to Form Devices

Devices may be fabricated from any biocompatible material or combination of materials that do not interfere with delivery of one or more active agents, assays performed, or data collection, if employed.

In certain embodiments, the device is radiopaque to facilitate imaging during implantation, residence, and/or removal. In some cases, one or more portions of the device are fabricated from a material, such as stainless steel, which is radiopaque. In some cases, one or more contrast agents are incorporated into the device to improve radiopacity or imaging of the device in vivo.

The microwells and support structure are generally fabricated from biocompatible materials that provide the device with suitable integrity to permit device implantation and removal, and to provide the desired residence time within the target tissue. In instances where the microwells, support structure, or both are fabricated from a non-biocompatible material, the non-biocompatible material is generally coated with another material to render the microwells and support structure biocompatible.

In some embodiments, the microwells and support structure are formed from a single material. In other embodiments, the microwells and support structure are formed from multiple materials that are combined so as to form an integral structure. Examples of materials that can be used to form the microwells and/or support structure include polymers, silicones, glasses, metals, ceramics, inorganic materials, and combinations thereof. In certain embodiments, the microwells and support structure are formed from composite materials, such as, for example, a composite of a polymer and a semiconductor material, such as silicon.

In some embodiments, the microwells, support structure, or combination thereof, are formed from or include a polymer. Examples of suitable polymers include polyacrylates, polymethacrylates, polycarbonates, polystyrenes, polyethylenes, polypropylenes, polyvinylchlorides, polytetrafluoroethylenes, fluorinated polymers, silicones such as polydimethylsiloxane (PDMS), polyvinylidene chloride, bis-benzocyclobutene (BCB), polyimides, fluorinated derivatives of polyimides, polyurethanes, poly(ethylene vinyl acetate), poly(alkylene oxides) such as poly(ethylene glycol) (PEG), or copolymers or blend thereof.

Although not preferred, in certain embodiments, microwells, support structure, or combination thereof, are fabricated from or include one or more biodegradable polymers. Examples of suitable biodegradable polymers include polyhydroxyacids, such as poly(lactic acid), poly(glycolic acid), and poly(lactic acid-co-glycolic acids); polyhydroxyalkanoates such as poly3-hydroxybutyrate or poly4-hydroxybutyrate; poly(caprolactones); poly(orthoesters); poly(phosphazenes); polyesteramides; polyanhydrides; poly(dioxanones); poly(alkylene alkylates); poly(hydroxyacid)/poly(alkylene oxide) copolymers; poly(caprolactone)/poly(alkylene oxide) copolymers; biodegradable polyurethanes; poly(amino acids); polyetheresters; polyacetals; polycyanoacrylates; poly(oxyethylene)/poly(oxypropylene) copolymers, or a blend or copolymer thereof, may be used. Biodegradable shape memory polymers, such as those described in U.S. Pat. No. 5,189,110 or 5,139,832, may also be employed.

In some embodiments, the microwells, support structure, or combination thereof, formed from or include a metal. Examples of suitable metals include, but are not limited to, cobalt, chromium, nickel, platinum, gold, silver, silicon, stainless steel, titanium, tantalum, and any of their alloys (e.g., nickel-titanium alloys), and combinations thereof. Biodegradable metals such as magnesium-based metals may also be used.

In particular embodiments, the microwells, support structure, or combination thereof are fabricated from or include silicon or a ceramic such as hydroxyapatite. In particular embodiments, the microwells, support structure, or combination thereof are fabricated from or include a polymer formed from SU-8, the structure of which is shown below.

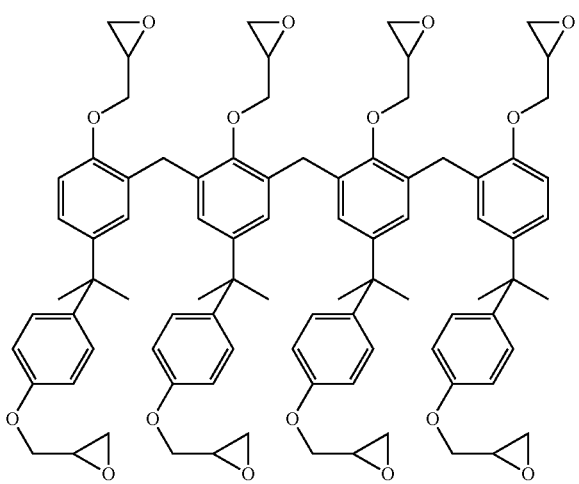 [SMILES: CC(C)(c1ccc(OCC2CO2)cc1)c1ccc(OCC2CO2)c(Cc2cc(C(C)(C)c3ccc(OCC4CO4)cc3)cc(Cc3cc(C(C)(C)c4ccc(OCC5CO5)cc4)cc(Cc4cc(C(C)(C)c5ccc(OCC6CO6)cc5)ccc4OCC4CO4)c3OCC3CO3)c2OCC2CO2)c1]

In some embodiments, the device includes an agent that prevents or reduces biofilm formation or inflammation or other foreign body reaction to the device once implanted. Such an agent may be incorporated within one or more of the component materials of the device, or coated on a surface the device, or portions thereof. In certain embodiments, one or more portions of the device is coated with a polymer coating to prevents or reduces biofilm formation or inflammation or other foreign body reaction to the device.

In preferred embodiments, the device is cylindrical in shape to facilitate implantation and minimize tissue damage. A representative example of a cylindrical device is illustrated in FIG. 1. The device (10) contains a support structure (16), forming the body of the device. The device has a proximal end (14) and a proximal end (12), from which a guidewire (20) extends, and a plurality of microwells (18) formed within the support structure. One or more of the microwells contain an active agent or agents (22), which can be released independently or in combination.

In the preferred embodiment, the device is formed of silicon, which has the advantages of being biocompatible, resistant to fracturing, easily manufactured with high resolution) or SU8 polyethylene, which has the advantage of being very biocompatible, and softer thereby allowing microtome sectioning.

Guidewires

In some embodiments, the device also includes a guidewire designed to assist in the implantation of the device at a site of medical interest and/or its subsequent removal from the site of implantation. The guidewire may be attached to or extend from any portion of the device. In certain embodiments, the guidewire extends from the proximal end of the device.

The guidewire can be any wire-like structure dimension and length which is suitable to assist in the implantation of the device at a site of medical interest and/or its subsequent removal from the site of implantation.

In certain embodiments, the guidewire has a diameter of between about 0.010 inches and about 0.065 inches. The length of the guidewire typically ranges from about 30 cm to about 300 cm (or more) in length; however, the guidewire is typically long enough to extend from the site of device implantation to a point outside of the patient's body, such that the guidewire remains externally accessible after implantation of the device.

Guidewires can be fabricated from any material or combination of materials, such as polymers, metals, and polymer-metal composites. Examples of suitable materials include metals, such stainless steel (e.g., 304 stainless steel), nickel and nickel alloys (e.g., NITINOL® or MP-35N), and cobalt alloys, polymers, such as polyurethanes, elastomeric polyamides, block polyamide-ethers, and silicones. Radiopaque alloys, such as platinum and titanium alloys, may also be used to fabricate, in whole or in part, the guidewire.

In certain embodiments, the guidewire is coated or treated with various polymers or other compounds in order to reduce foreign body reaction provide or to provide desired handling or performance characteristics such as to increase lubricity. In certain embodiments, the guidewire is coated with polytetrafluoroethylene (PTFE) or a hydrophilic polymer coating, such as poly(caprolactone), to enhance lubricity and impart desirable handling characteristics to the guidewire.

Sensors; Fiber Optics

In some embodiments, the device also includes a fiber optic bundle, or other interrogatable or addressible means extending from a portion of the microassay device. The length of the fiber optic bundle typically ranges from about 30 cm to about 300 cm (or more) in length; however, the fiber optic bundle is typically long enough to extend from the site of device implantation to a point outside of the patient's body, such that the fiber optic bundle remains externally accessible after implantation of the device.

In these embodiments, individual fiber optic elements within the fiber optic bundle may by internally wired to one or more of the microwells in the miroassay device. The fiber optic elements can be interfaced with external signal processing means to analyze the contents of the microwells, the nature of tissue proximal to the microwells, and combinations thereof. The fiber optic elements can also be interfaces with an external energy source to trigger the release of a drug or to provide photodynamic therapy.

The interrogatable means may be connected to sensors adjacent to or within the microwells. These may also have means for remote accessing, such as a WiFi connection.

Figure 2:
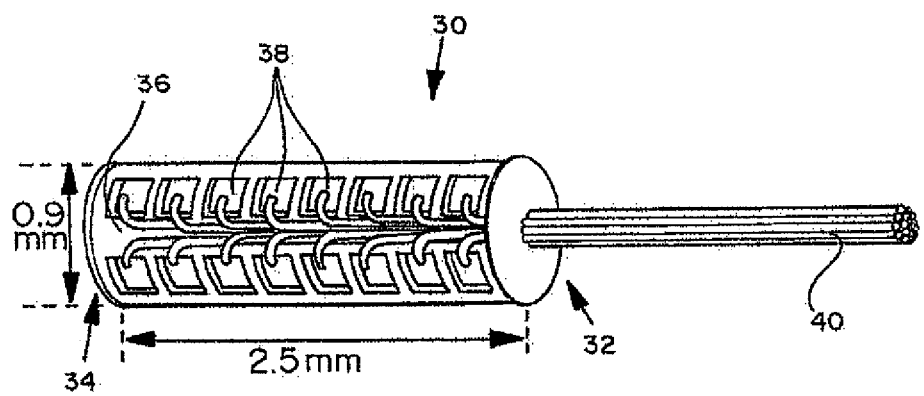
FIG. 2 is a cutaway diagram of a cylindrical device containing a fiber optic bundle extending from the proximal end of the cylindrical device. Fiber optic elements are internally connected to each of the microwells in the device.

FIG. 2 illustrates a cylindrical device containing integrated fiber optic components. In this embodiment, the device (30) contains a support structure (36), forming the body of the device. The device has a distal end (34) and a proximal end (32), from which a fiber optic bundle (40) extends, and a plurality of microwells (38) formed within the support structure. Individual fiber optic elements within the fiber optic bundle are internally wired to the microwells in the miroassay device.

Tissue Retainers

In some embodiments, the device also contains a feature, such as an overhang or lip, to facilitate the removal of a tissue sample immediately surrounding the device upon device removal. The device may also include retainers that are recessed into the device until implantation or removal. These are then expanded outwardly into the tissue where they can serve to stabilize or maintain the spatial arrangement of the tissue relative to the device and/or decrease any overlap in drug diffusion between wells.

The device can also contain a fastening means, such as a snap-lock fastener, or a magnet at the proximal end of the device to facilitate device removal.

B. Active Agents

One or more active agents are incorporated in one or more of the microwells in the devices. In some devices, all of the microwells contain one or more active agents, in one or more dosages. In other devices, not all of the microwells contain an active agent. In these embodiments, empty microwells may serve as a control, or increase distance between released drug to decrease overlap in diffused drug.

In some embodiments, each microwell which contains an active agent contains a different active agent or different combination of active agents. In some embodiments, a plurality of microwells each contains an active agent or combination of active agents in differing amounts of active agents, differing ratios of active agents, or different excipients/formulations of active agents. This allows variation not only of the drug, but also the dosage, release pharmacokinetics, and testing of various combinations at the same.

The devices deliver a microdose amount of a substance to a target tissue. A microdose amount may be from about 0.001 µg (or less) to about 1,000 µg, or about 10,000 µg (or more) of the substance. Those of skill will readily appreciate that microdose levels may vary as a function of the specific substance employed, the target tissue, and/or the medical condition being treated. Appropriate doses may be determined as described in example 1.

The substance may be delivered in a controlled release, sustained release, delayed release, or pulsatile fashion. Delivery may also occur over any time period. For example, it may occur over a period of minutes to hours, or days to weeks. In the preferred embodiment, release is complete within 48 hours, with substantially all drug being released within 12, 24, 36, or 48 hours.

The drug may be applied as a powder, particulate, or in a solution or suspension, with the solvent removed by drying, evaporation, lyophilization or suction. A membrane or film may be applied to the well after the drug is incorporated to isolate the drug until the time of use. Alternatively, a porous membrane may be used to cover the microwells to control rate of release after implantation. The drug may be held within a matrix formed of a biodegradable material or a material which releases the incorporated substance by diffusion out of or degradation of the matrix, or by dissolution of the substance into surrounding interstitial fluid. When provided in a matrix, the substance may be homogeneously or heterogeneously distributed within the matrix.

Selection of the matrix may be dependent on the desired rate of release of the substance. Both biodegradable and nonbiodegradable matrices (release systems) can be used for delivery of the substances. Suitable release systems include, without limitation, polymers and polymeric matrices, non-polymeric matrices, or inorganic and organic excipients and diluents such as, but not limited to, calcium carbonate and sugar. The release systems may be natural or synthetic. In some variations, the release system may be selected based on the period over which release is desired. Drugs from wells can be released not only with distinct drugs and concentrations, but also at different kinetics, depending on (potentially) a different material coating in each well (such as platinum or gold or polymer).

In preferred embodiments, the active agent is an anti-neoplastic agent. Representative anti-neoplastic agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), and topoisomerase inhibitors (including camptothecins such as camptothecin, irinotecan, and topotecan as well as derivatives of epipodophyllotoxins such as amsacrine, etoposide, etoposide phosphate, and teniposide).

Other drugs may be anti-infectives such as antivirals, antibiotics, or antifungals, immunomodulators, either immunoenhancers, vaccines, or immunosuppressants, or hormones or analogues, agonists or antagonists thereof.

Active agents may be small molecule active agents or larger molecules (e.g., macromolecules) such as proteins, peptides, carbohydrates and nucleic acids. A preferred class of protein is antibodies and fusion proteins. "Small Molecule", as used herein, refers to a molecule, such as an organic or organometallic compound, with a molecular weight of less than 2,000 Daltons, more preferably less than 1,500 Daltons, most preferably less than 1,000 Daltons. The small molecule can be a hydrophilic, hydrophobic, or amphiphilic compound.

C. Methods of Manufacture

Devices can be fabricated using methods known in the art, such as patterning, photolithography and etching. Suitable methods for the manufacture of devices can be selected in view of a variety of factors, including the design of the device (e.g., the size of the device, the relative arrangement of device features, etc.) and the component materials used to form the device.

Examples of suitable techniques that can be used, alone or in combination, for the fabrication of devices include LIGA (Lithographic Galvanoforming Abforming) techniques using X-ray lithography, high-aspect-ratio photolithography using a photoresist, such as an epoxy-based negative photoresist such as EPON™ SU-8 (also referred to as EPIKOTE™ 157), microelectro-discharge machining (µEDM), high-aspect-ratio machining by deep reactive ion etching (DRIE), hot embossing, 3-dimensional printing, stereolithography, laser machining, ion beam machining, and mechanical micro-cutting using micro-tools made of hard materials such as diamond.

Detailed methods for microfabrication are described in, for example, "Microreactors, Epoch-making Technology for Synthesis" (edited by Jun-ichi Yoshida and published by CMC Publishing Co., Ltd., 2003) and "Fine Processing Technology, Application Volume—Application to Photonics, Electronics and Mechatronics—" (edited by the Meeting Committee of the Society of Polymer Science, Japan, and published by NTS Inc., 2003.

III. Methods of Use

The device is implanted directly into a tumor or other tissue to be treated. The tissue will typically be transformed, i.e. cancerous tissue, but may also be infected with bacteria, fungus or virus, in need of immunomodulation (i.e., immunosuppression or immunoenhancement), or in need of hormonal adjustment. In some cases the hormone may be useful for treating a cancer. The device is particularly useful in treating refractory disorders and in testing combination of drugs that may be more effective in combination.

The device releases an array of drug micro doses locally, and uses state of the art detection methods to identify the drugs or combinations inducing a response. By using micro doses of drugs, the device is capable of testing each patient for response to large range of regimens, without inducing systemic toxicities. These data can be used along with genomic data to accurately predict systemic drug response.

In some variations, a microdose amount is used in early human studies, e.g., before a phase I clinical trial, to evaluate the effect of the substance on a target tissue, or to obtain pharmacokinetic or metabolic data. In other variations, a microdose amount is used to locally treat a medical condition, e.g., a cancer or tumor. In yet other variations, a microdose amount is used to locally deliver a contrast agent for a structural or functional imaging procedure. In view of this, a microdose amount can be tailored to the specific indication of the substance delivery.

The assay may be used to detect one or more of: a degree of agent permeation through the target tissue; detect a physiochemical effect of the agent on the target tissue; and detect a pharmacological effect of the agent on the tissue. In further variations, the devices may include a sensor for sensing one or more parameters of the target tissue after delivery of the substance. An agent may be delivered as a result of the response parameter or in response to the data obtained by the assay and/or sensor. The assay may be configured to provide various data such as data related to efficacy such as chemotherapeutic efficacy; activity such as tumor cell invasiveness; toxicity such as toxicity due to one or more agents being delivered or toxicity due to cell death; and combinations of these.

A. Target Tissues

The target tissue may be located anywhere in the patient's body such as locations including: liver, lung, kidney, prostate, ovary, spleen, lymph node, thyroid, pancreas, heart, skeletal muscle, intestine, larynx, esophagus and stomach. In a preferred embodiment, the target tissue is tumor tissue including but not limited to: adenoma, adenocarcinoma, squamous cell carcinoma, basal cell carcinoma, small cell carcinoma, large cell undifferentiated carcinoma, chondrosarcoma, fibrosarcoma, and combinations thereof.

The target tissue may also be a tissue which is infected, for example, with a virus, bacteria, fungus or parasite, or which is characterized by inflammation or is in need of immunostimulation.

B. Delivery and Retrieval of the Device

Devices may be implanted via percutaneous, minimally invasive, or open procedures into the tissue of a patient. For example, devices may be delivered via an open surgical procedure, or by a minimally invasive procedure such as laparoscopy, endoscopy, arthroscopy, and catheter-based procedures. The devices may also be delivered percutaneously, for example using a needle, such as a 19 to 24 gauge biopsy needle. Retrieval of the devices may occur via the same processes, typically also using a biopsy needle with but with a larger diameter, such as a 16 to 18 gauge needle. The inserting needle is a cutting needle that has a smaller diameter than the retrieval needle, which is a larger diameter coring needle.

An image of the target tissue, such as a tumor, may be performed prior to implantation, during implantation, during implant residence, during implant removal, after implant retrieval, and combinations thereof. In certain embodiments, the microassay device is implanted in the patient with image guidance.

In most cases, the device is implanted into a tumor using a biopsy-type needle, cannula, catheter or stylet. The device can also be placed in a lumen, such as a bile duct, alveoli or bronchi or kidney tubule. Alternatively, the device can be placed during a procedure such as a biopsy or excision of tumor.

In the preferred embodiment, the device is placed using a cutting biopsy needle with sharp stuffer tip. The stuffer needles are then retracted while keeping the needle in place. The device is delivered through the needle, then the need is retracted. A guidewire may be attached prior to or at the time of implantation. The advantage of this method is that there is better tissue penetration into the wells, and less tissue injury.

The device is retrieved in conjunction with the adjacent tissue. The goal is to analyze the tissue in the spatial orientation relevant to the device, to allow assessment of efficacy, dose dependency, and type of response (i.e., apoptosis, necrosis, inflammation, subclinical response). In a preferred embodiment, the device is retrieved by excising the device and associated tissue at one time, for example, by cutting out the device with a uniform amount of tissue around the device. In the case of a cylindrical device, one excises the device using a cutting needle or catheter that is of a greater diameter than the device. The guidewire may be used to insure that the tissue remains placed in the same proximity to the device. Stabilizers or retainers may be used in either the cutting removal device or the implanted device to help maintain spatial relationship with the device and treated tissue.

C. Analysis of Tissue

Following retrieval, usually less than 7 days from implantation, the treated tissue samples are analyzed, for example, by microscopic examination, by enzyme assays, and other histology and immunohistochemistry techniques used to assess cancer or infected cells.

Figure 3:
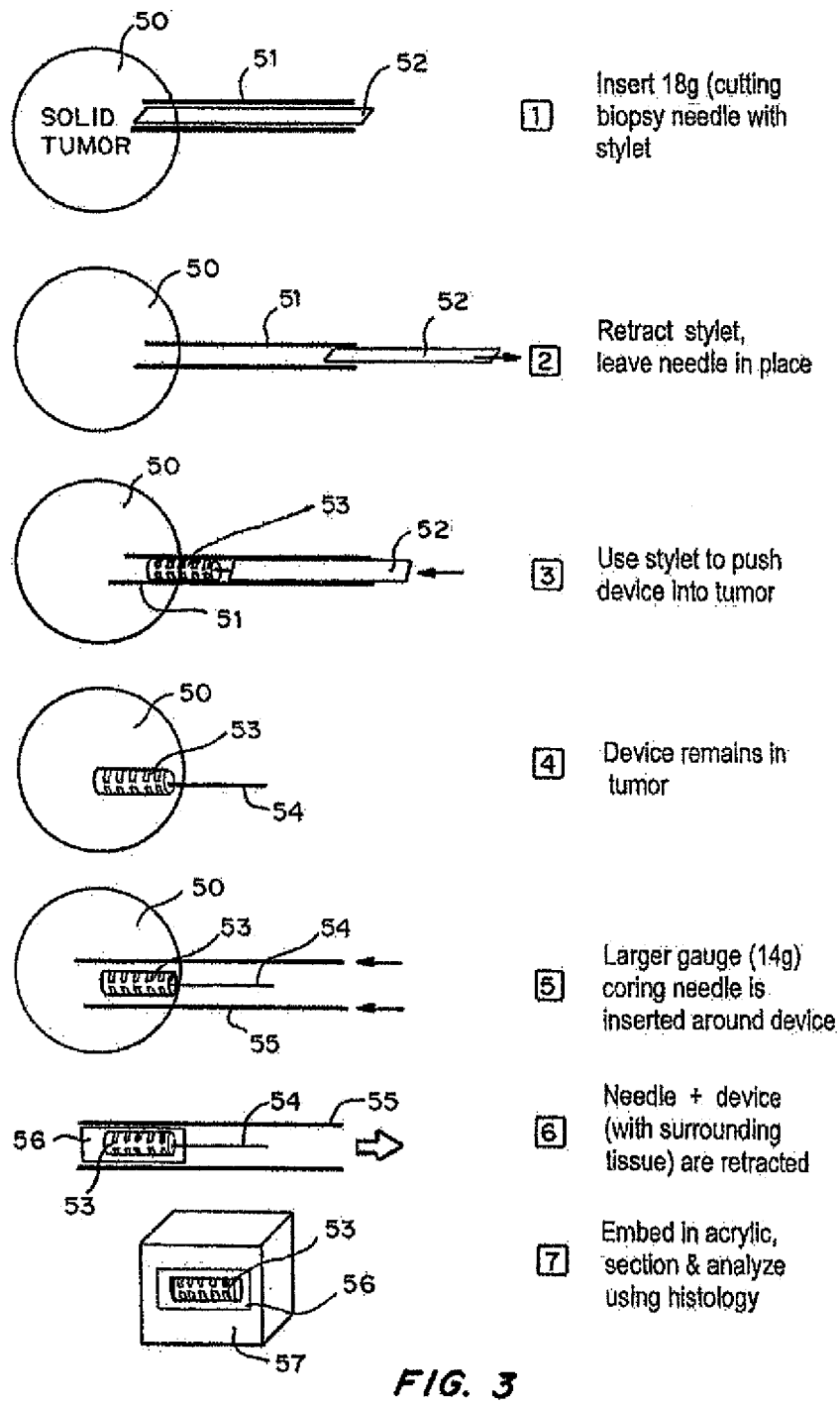
FIG. 3 illustrates an in vivo method for analyzing the sensitivity of solid tumor a patient to one or more active agents.

FIG. 3 illustrates an in vivo method for analyzing the sensitivity of solid tumor a patient to one or more active agents. An 18 g cutting biopsy needle 51 with stylet 52 is inserted into a solid tumor 50. The stylet 52 is retracted, leaving the needle 51 in place. The stylet 52 is used to push the device 53 into the tumor 50. The device 53 remains in the tumor 50 except for a retrieving device 54. A larger 14 gauge coring needle 55 is inserted into the tumor 50 around the device 53. The needle 55 is retracted, taking the device 53 and surrounding tissue 56. The device 53 is then embedded in acrylic 57, sectioned and histology preformed.

Figure 4A:
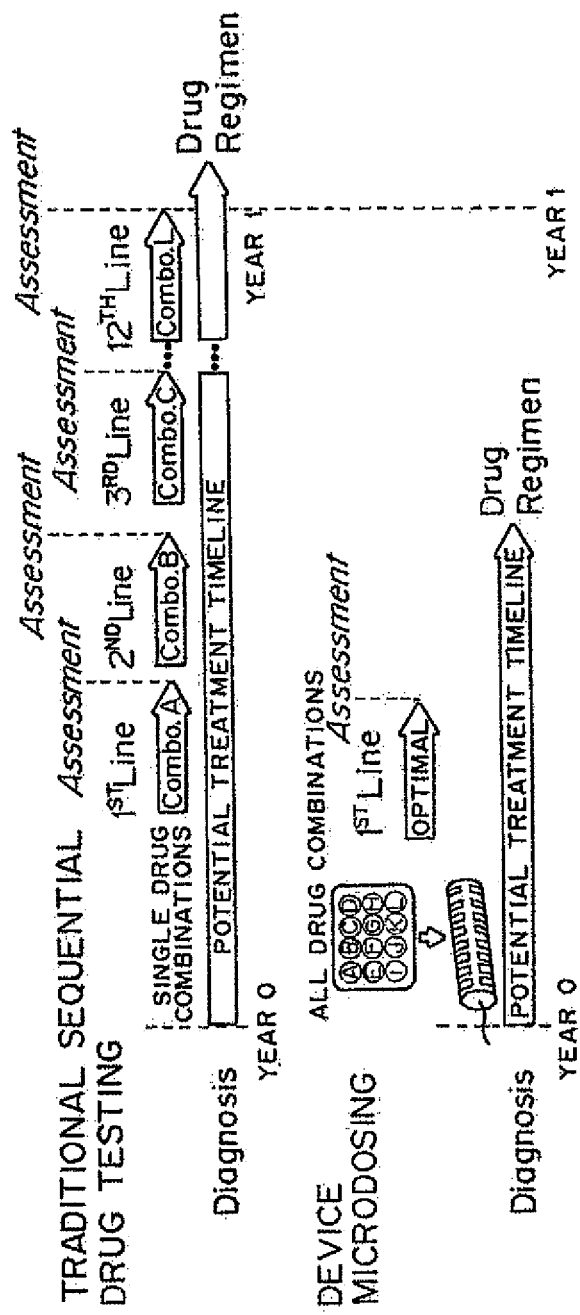

FIGS. 4A-D are schematics showing the arrangement of drugs in wells in the device (FIG. 4A), implantation (FIG. 4B), dosing where drug is released from the wells (FIG. 4C), and the different results obtained (FIG. 4D).

IV. Kits

Kits may contain one or more of the devices described above. Any number and type of deployment tools, retrieval tools, and imaging devices may also be included. The kits may also contain additional in vitro assays for evaluating samples, such as a matrix for fixing tissue samples for future histological analysis.

The kits may also include instructions for using the devices, tools, and/or assays contained therein.

EXAMPLES

Example 1: Prototype Testing in Mouse Model

Materials and Methods

As shown in FIG. 5, a mouse model for a human cancer cell line is prepared by injection of human cancer cells such as MDA MB-231 into the mammary fat pad of an immunodeficient mouse. Tumors are allowed to implant and proliferate to approximately 150-170 $mm^3$.

Individual drugs are administered systemically by injection to the mice to establish local pharmacokinetics for the drugs. For breast cancer cells, representative drugs to be tested include docetaxel, doxorubicin, irinotecan, transtuzumab, and bevacizumab.

The device can be loaded with the same drugs based on the results of the systemic testing. Each drug is loaded separately and in more than one concentration, as well as in combination. After 12, 24, 36 and 48 hours, devices are removed and histology conducted to look at the effect on the tumor cells adjacent to each well.

Analysis for apoptosis, necrosis, mitotic cell death, and proliferation can also be conducted. The local microdose response is then determined and can be used to define an appropriate therapeutic regime for the cancer.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An implantable microdevice comprising
a cylindrical support structure having on its curved surface and along the length of the cylindrical support structure a plurality of microwells formed on or within the support structure, the plurality of microwells containing up to a microdose of one or more active agents,
the implantable microdevice having a diameter of between about 0.5 mm and about 2.0 mm, and a length of less than about 5.0 mm, which permit implantation into a tissue using a catheter, cannula, or biopsy needle and removal of the microdevice with the adjacent tissue in spatial orientation with the implantable microdevice using a catheter, cannula, or a biopsy needle with a larger diameter than that of the microdevice,
optionally comprising a guidewire attached to a proximal end of the microdevice.

2. The microdevice of claim 1 wherein the one or more active agents comprises a plurality of active agents, combinations of active agents or active agents with plurality of concentrations or release pharmacokinetics thereof.

3. The microdevice of claim 1 formed by a method selected from the group consisting of lithographic galvanoforming abforming (LIGA), high-aspect-ratio photolithography using a photoresist, microelectro-discharge machining, high-aspect-ratio machining by deep reactive ion etching (DIRE), hot embossing, 3-dimensional printing, stereolithography, laser machining, ion beam machining, and mechanical micro-cutting.

4. The microdevice of claim 1 comprising a guidewire attached to an end of the device, one or more sensors integrated within the implantable microdevice or microwells, and fiber optic or other addressible or interactive means for remote interrogation of the implantable microdevice.

5. The microdevice of claim 1 comprising means for maintaining tissue in a spatial orientation to the microdevice at the time of or after removal of the implantable microdevice.

6. A kit comprising the microdevice of claim 1 and means for insertion or means for removal.

7. The kit of claim 6, wherein the one or more active agents comprises a plurality of active agents, combinations of active agents or active agents with plurality of concentrations or release pharmacokinetics thereof.

8. The kit of claim 6, wherein the microdevice comprises a guidewire attached to an end of the microdevice, one or more sensors integrated within the implantable microdevice or microwells, and fiber optic or other addressible or interactive means for remote interrogation of the microdevice.

9. The kit of claim 6, wherein the microdevice comprises means for maintaining tissue in a spatial orientation to the microdevice at the time of or after removal of the microdevice.

10. The kit of claim 6 wherein the means for insertion is a biopsy cutting needle between 19 and 24 gauge.

11. The kit of claim 6 wherein the means for removal is a biopsy coring needle between 14 and 18 gauge.

12. The kit of claim 6 comprising a sensor for evaluating tissue samples.

13. The implantable microdevice of claim 1, comprising one or more sensors integrated within the implantable microdevice or microwells, and fiber optic or other addressible or interactive means for remote interrogation of the microdevice.

14. A method for assaying tissue for an effective active agent, effective dosage, effective pharmacokinetics of an active agent, or a combination thereof, comprising implanting in a tissue an implantable microdevice and assaying for at least one analyte or removing tissue for analysis,
the implantable microdevice comprising
a cylindrical support structure having on its curved surface and along the length of the cylindrical support structure a plurality of microwells formed on or within the support structure,
the microwells containing up to a microdose of one or more active agents,
the implantable microdevice having a diameter of between about 0.5 mm and about 2.0 mm, and a length of less than about 5.0 mm, which permits implantation into a tissue using a catheter, cannula, or biopsy needle and removal of the microdevice with the adjacent tissue in spatial orientation with the implantable microdevice using a catheter, cannula, or a biopsy needle with a larger diameter than that of the microdevice,
optionally comprising a guidewire attached to a proximal end of the microdevice.

15. The method of claim 14 comprising removing the microdevice and adjacent tissue and analyzing the tissue.

16. The method of claim 14 wherein the tissue is a tumor.

17. The method of claim 14 wherein the tissue is infected or in need of immunomodulation or hormonal treatment.

* * * * *